US 7,507,372 B2

(12) United States Patent
Polak

(10) Patent No.: US 7,507,372 B2
(45) Date of Patent: Mar. 24, 2009

(54) METHOD FOR FLUSHING PARTICLE-BEARING FILTER BEDS, TO STERILIZE AND DECONTAMINATE THE SAME

(75) Inventor: Walter Polak, Salzburg (AT)

(73) Assignee: P&W Invest Vermogensverwaltungsges MBH, Salzburg (AT)

( * ) Notice: Subject to any disclaimer, the term of this patent is extended or adjusted under 35 U.S.C. 154(b) by 659 days.

(21) Appl. No.: 10/220,341

(22) PCT Filed: Feb. 22, 2001

(86) PCT No.: PCT/EP01/02030

§ 371 (c)(1),
(2), (4) Date: May 9, 2003

(87) PCT Pub. No.: WO01/64310

PCT Pub. Date: Sep. 7, 2001

(65) Prior Publication Data

US 2004/0105781 A1 Jun. 3, 2004

(30) Foreign Application Priority Data

Mar. 2, 2000 (DE) ................. 100 10 255

(51) Int. Cl.
*A61L 2/18* (2006.01)
*A61L 2/00* (2006.01)

(52) U.S. Cl. .......................................... 422/37; 422/28
(58) Field of Classification Search .................. 422/37, 422/38
See application file for complete search history.

(56) References Cited

U.S. PATENT DOCUMENTS

| 4,049,545 A | * | 9/1977 | Horvath | ....................... 210/665 |
| 4,104,163 A | * | 8/1978 | Grutsch | ....................... 210/794 |
| 4,574,084 A | * | 3/1986 | Berger | ......................... 424/601 |

FOREIGN PATENT DOCUMENTS

| DE | 3403 631 A1 | 8/1984 |
| EP | 0 104 341 A2 | 4/1984 |
| FR | 853 566 | 1/1977 |
| JP | 405168873 A | * | 7/1993 | ................. 210/108 |

\* cited by examiner

*Primary Examiner*—Elizabeth L McKane
*Assistant Examiner*—Kevin C Joyner
(74) *Attorney, Agent, or Firm*—Fay Sharpe LLP; Karl W. Hauber

(57) ABSTRACT

The present disclosure provides a method for flushing particle bearing filter beds located in a circuit or linear water treatment plant for sterilization and decontamination of the filter beds. The filter can be charged with a chlorine-oxide-containing, chlorine-dioxide-containing, halogen-containing, and/or peroxide-containing aqueous solution. A solution acts on the deposits of the particle-type filter bed such that the bed can be subsequently flushed with water and/or an aqueous medium for removal of the process caused reaction product and any residual chlorine oxides or halogens or peroxides.

16 Claims, No Drawings

METHOD FOR FLUSHING PARTICLE-BEARING FILTER BEDS, TO STERILIZE AND DECONTAMINATE THE SAME

The invention relates to a method for flushing particle-bearing filter beds which are located in circuit or linear water treatment plants, to sterilize and decontaminate same.

When treating water in circuit or linear treatment plants, filtration of water represents an important and basic process step. First and foremost, solid particles which are contained in the unfiltered water are meant to be retained by the filter bed. In general, the filter bed consists of materials such as pebble stones, sand, fire clay mortar, zeolites or carbon-containing materials, upon which or between which solid matter or flocculated substances become deposited. These deposits require that the filter bed be cleaned in regular intervals. In general, but not with all systems, water is used during the filtration procedure, which is pumped in the opposite direction, compared with the flow direction of the water. This step is called flushing or filter flushing. For flushing purposes, it is also possible to employ air and water/air mixtures, either individually or in combination with each other.

In addition to the formation of deposits having organic or inorganic origin, with increasing operating time of the filter bed, there frequently also occurs contamination of the filter materials with microorganisms, among which may also be some pathogenic germs. Tests have shown that approximately 80 to 90% of filter materials, in particular in the lower region of the layer of filter material, are burdened in large degree by germs and biogenic deposits (bio-films). Aside from the filter material, this also pertains to the surfaces of the filtrate chamber as well as the filtration nozzles, including the walls of the flush water basin. As a consequence, there may result significant problems relative to hygiene, for example with respect to swimming pool and bathing pool water—that is to say—even though in this instance the bather comes only into direct contact with pool water, contamination of the filter with microorganisms poses a significant risk, since, for example, with sudden decreasing germicidal capacity of the pool water, large quantities of germs may rapidly get from the affected filter into the pool water.

DE-A-32 33 857 describes a method and a device for the cleaning of filter elements, wherein a mixture of water and a pre-tensioned gas are being used. If applicable, the gas portion of the mixture is enriched with a surface-active agent in order to lower the surface tension of the water, so that a more homogenous flushing medium mixture is obtained.

DE-32 29 219 describes the use of a border line-active substance as reverse flushing agent for particle-containing reverse-flushable filter beds in the treatment of water for swimming pool treatment plants, potable water treatment plants and sewage water treatment plants. With this method, however, the purification effect is only average in comparison to solid deposits. In particular, only low-level effect is achieved vis-a-vis contamination of the filter by means of microorganisms and biogenic deposits. In addition, the border-line active substances must be applied in high concentration, which leads to high costs and high burden of the sewage water.

Therefore, it was the object of the present invention to make available a method which avoids the aforementioned drawbacks. In particular, the inventive method, aside from high purification effect vis-a-vis organic and inorganic solid deposits in the filter bed was to also permit effective decontamination of the entire filter with respect to microorganisms and biogenic deposits and, at the same time, it was to be cost-beneficial and lead to only low-level burdenings of the sewage water.

According to the invention, said object is solved in that an aqueous solution containing chlorine oxide and/or halogen and/or peroxide is left to act on the deposits of the particle-type filter bed and subsequently said bed is then flushed with water or an aqueous medium for removal of process-caused reaction products as well as the remaining chlorine oxide and/or halogen and/or peroxide.

Essential characteristic of the inventive method is, therefore, a two-stage method of procedure.

In the first step of the procedure, the filter is charged with the chlorine oxide-containing and/or halogen-containing and/or peroxide-containing aqueous solution, which is subsequently left to act on the filtering material. In the second step of the procedure, flushing of the filter takes place with water and/or an aqueous medium.

The inventive method is particularly appropriate for application in circuit water treatment plants such as swimming pool circuits, cooling water circuits and industrial water circuits and linear water treatment plants, such as potable water and sewage water treatment plants.

It has proven particularly beneficial that the chlorine-oxide, and/or halogen-containing and/or peroxide-containing aqueous solution is left to act upon the deposits of the particle-type filter bed for approximately 1 to 3 hours. Under certain circumstances, shorter intervals may be sufficient and/or longer intervals may be necessary.

For reasons of effectiveness as well as reasons of accessibility, chlorine di-oxide is particularly preferred among the chlorine oxides, so that with respect to the chlorine-oxide-containing solution employed in the inventive method, the preferable solution involves an aqueous, chlorine-di-oxide-containing solution. It has been shown that the oxidative properties of the chlorine dioxide lead to high effectiveness of the method according to the invention. Since the chlorine di-oxide is an unstable and difficult to handle substance, it is of benefit that a large portion of the chlorine di-oxide is not present in free form in the solution, but in chemically bound form of a chemical species from which is formed a constant additional supply of chlorine di-oxide.

Such a substance is tetra-chlorine-deca-oxide-complex-di-anion $[Cl_4O_{10}]^{2-}$, which is documented under ELINCS No. 420-970-2. The tetra-chlorine-deca-oxide-complex-dianion is in equilibrium with the chlorine di-oxide, so that a solution of the tetra-chlorine-deca-oxide-complex-dianion always contains a certain amount of chlorine di-oxide, which is then formed again upon its consumption.

In a preferred specific embodiment, tetra-chlorine-deca-oxide-complex-dianion $[Cl_4O_{10}]^{2-}$ is, therefore, present in the chlorine di-oxide-containing aqueous solution.

The solution containing tetra-chlorine-deca-oxide-complex-dianions and chlorine-di-oxide is preferably obtained in that a sulfations-containing aqueous solution having a pH value $\leq 3$ is reacted with a therein stable peroxy-compound and said solution is subsequently mixed with the aqueous alkaline solution of a chlorite. Preferably the sulfations-containing aqueous solution is mixed in such a quantity of a therein stable peroxy compound that the final product is a peroxy compound concentration of approximately 0.001 to 0.01 molar. This is especially of advantage if the sulfations-containing aqueous solution is mixed with the therein stable peroxy compound and said solution is subsequently mixed with the aqueous alkaline solution of a chlorite in an amount so that a pH-value is attained of higher than 7.0, in particular ranging between 7.5 and 8.0.

Depending upon the degree of pollution and/or bacterial contamination of the filter, the invention-specific method can be employed with variable concentrations of the described solutions containing tetra-chlorine-deca-oxide-complex-dianions and chlorine-di-oxide. In a preferred specific embodiment, the solution is left to act upon the deposits of the particle-type filter bed in a concentration which corresponds to an initial concentration of chlorite of approximately 5 to 20 mmol/l.

It has proven itself as particularly beneficial to use as peroxy compound an inorganic peroxy compound in form of hydrogen peroxide, a persulfate, percarbonate, perborate, or a peroxide of an alkali- or an alkaline-earth metal. As chlorite, preferable use is made of an alkali- and/or alkaline-earth chlorite. Particularly beneficial results are attained if the sulfations-containing aqueous solution presents a pH value of $\leq 1$.

If the employed aqueous starter solutions present only low carbonate hardness, and/or are produced with de-mineralized water, it is suggested that the work be done under inert gas atmosphere, inasmuch as absent a protective gas layer, explosive air/chlorine di-oxide mixtures may be formed between the low gas emitting chlorine di-oxide and the air. Air/chlorine di-oxide mixtures tend to produce, at a ratio of air to chlorine di-oxide of 10:1, explosion-like decomposition of the chlorine di-oxide into chlorine and oxygen. With aqueous starter solutions of medium and/or high carbonate hardness (>approximately 7 degree and/or >approximately 1.3 mmol/l carbonate hardness) application of an inert gas is generally not required, since a type of protective gas layer is formed of carbon di-oxide. Preferably, therefore, mineralized water is used for the preparation of the sulfations-containing aqueous solution which is to be employed for the formation of the solution which contains tetra-chlorine-deca-oxide-complex-dianions and chlorine-di-oxide.

The solution containing tetra-chlorine-deca-oxide-complex-dianions and chlorine-di-oxide preferably contains a water-soluble phosphate, since it is possible to reduce the amount of peroxy compounds if a water-soluble phosphate, for example sodium-metapolyphosphate is incorporated in small amount in the finished solution.

The invention-specific method is suitable for sterilizing and decontamination flushing of particle-bearing filter beds of different types in circuit and linear water treatment plants. In principle, there are no restrictions with respect to type, size and construction of the filter beds. With particle-bearing filter beds, we are preferably dealing with single/multi-layer filters, which comprise filter materials of quartz, gravel and/or sand and/or porous filter materials, such as fire brick mortar, zeolites and/or carbon-containing materials, such as activated carbon, lignite and anthracite coal. If particularly thorough removal of chlorine and/or chlorine di-oxide is sought in the second step of the process, it is possible to employ, instead of water, an aqueous solution of a thiosulfate (for example sodium thiosulfate). Beneficial use is made in this case of approximately 5.3 grams of thiosulfate for each gram of chlorine and approximately 3.0 grams of thiosulfate for each gram of chlorine di-oxide.

In summary, it can be stated that the invention-specific method makes possible sterilizing and purifying flushing of particle-containing filter beds of circuit and linear water treatment plants, which, when compared with the state of the art, leads to greatly improved results. Thus, the cleaning effect vis-a-vis organic and inorganic deposits is clearly improved. Particularly obvious are the benefits with respect to the, effect vis-a-vis contamination by microorganisms and biogenic deposits (bio films). The cleaning methods described in the art of the art only show weak effect in this respect.

It came as a surprise that the inventive method results not only in extensive decontamination of the treated filter beds insofar as being affected by microorganisms and biogenic deposits is concerned, but it also achieves strong preventive effect, in particular with respect to porous filter materials. The possible cause for this may be that as a result of killing all germs and the concurrent removal of all contaminants that might promote the growth of the microorganisms in that these microorganisms might serve, for example, as source of food, so that expansion of microorganisms is prevented over an extended time period, following the treatment. Application of the invention-specific method can therefore be considered and implemented as a preventive measure. It is, however, also suitable in the sense of an "immediate measure" for sanitary restoration of filter material. In addition, the invention-specific method is connected with low costs and does not result in significant burdening of sewage water.

In the following, the invention is explained in more detail, making use of examples:

EXAMPLE 1

Preparation of a Solution Containing tetra-chlorine-deca-oxide-complex-dianions and Chlorine di-oxide To 1 liter of sulfate-containing water (carbonate hardness: 18 degrees and/or 3.2 mmol/l) with a pH value of 0.5, are added 0.5 gr of a 30% by weight hydrogen peroxide solution. To said solution is added, under thorough stirring, 0.9 l of a commercial sodium chlorite solution (approximately 300 gr sodium chlorite/l). The solution undergoes a brownish coloration, which turns into a bright green color, after completion of stabilization reaction when the pH value exceeds 7. The solution adjusts itself to a pH value of 7.5.

EXAMPLE 2

Treatment of a Multi-Layer Filter with Carbon Material for Purification of Swimming and Bathing Pool Water According to the Invention-Specific Method.

The filter used in this example is a typical filter employed for purification of water in outdoor and indoor swimming pools.

It is characterized by the following standard sizes:

| | |
|---|---|
| Height | 2.5 m |
| Diameter | 2.1 m |
| Volume of Filter Bed | 5.2 m$^3$ |

Material of Filter Cover glass-fiber reinforced plastic material

Material of Filter Charge 4 layers of quartz gravel with decreasing granular size in upward direction and a top filter layer of granulated coal material.

The inventive flushing method was applied as follows with respect to the described filter:

To start with, the filter is flushed in normal fashion with water, and subsequently the filter vessel is emptied of water. After that, 6.7 liter of the solution containing tetra-chlorine-deca-oxide-complex-dianion, as described in Example 1, and chlorine dioxide are feed into the filter by means of a dosing pump, starting from the bottom. The filter is then fully filled with water from the bottom. After the filter has been fully charged, one waits approximately 1 and one half hours for effect to take place. After said time, the filter is flushed with water, using a flushing speed of approximately 40 m/h for a period of 10 minutes.

The invention claimed is:

1. Method for flushing particle-bearing filter beds located in circuit or linear water treatment plants for sterilization and decontamination of said filter beds, wherein the filter is charged with a chlorine dioxide containing aqueous solution, which acts on the deposits of the particle-type filter bed with said bed thereafter being subsequently flushed with water and/or an aqueous medium for removal of the process-caused reaction products and any residual chlorine dioxides;

wherein the chlorine-dioxide aqueous solution charges the filter and acts upon the deposits of the particle-type filter bed for a period of time prior to said flushing;

wherein the chlorine dioxide-containing aqueous solution is obtained in that a sulfations-containing aqueous solution having a pH value less than or equal to 3 is mixed with a therein stable peroxy compound and said solution is subsequently mixed with the aqueous alkaline solution of a chlorite;

wherein the particle-bearing filter bed involves single-/multi-layer filters, which contain quartz, gravel, sand, porous filter materials, and/or carbonaceous materials; and, wherein tetra-chlorine-deca-oxide-complex-dianion $[Cl_4O_{10}]^{2-}$ is present in the chlorine dioxide-containing aqueous solution and is in equilibrium with said chlorine dioxide such that said chlorine dioxide is formed during consumption from said aqueous solution.

2. Method according to claim 1 wherein the chlorine-dioxide aqueous solution acts upon the deposits of the particle-type filter bed for approximately 1 to 3 hours.

3. Method according to claim 1 wherein the sulfations-containing aqueous solution is mixed in such quantity of a therein stable peroxy compound that the final product has a peroxy compound concentration of approximately 0.001 to 0.01 molar.

4. Method according to claim 1 wherein the sulfations-containing aqueous solution is mixed with a therein stable peroxy compound and said solution is subsequently mixed with the aqueous alkaline solution of chlorites in an amount such that the pH value adjusts to higher than 7.

5. Method according to claim 1 wherein the chlorine-dioxide-containing aqueous solution is left to act upon the deposits of the particle-shaped filter bed in a concentration which corresponds to an initial chlorite concentration of approximately 5 to 20 mmol/l.

6. Method according to claim 1 wherein the peroxy compound is an inorganic peroxy compound used in the form of hydrogen peroxide, a persulfate, percarbonate, perborate or a peroxide of an alkaline or alkaline earth metal.

7. Method according to claim 1 wherein an alkaline and/or alkaline earth chlorite is employed as chlorite.

8. Method according to claim 1 wherein the sulfations-containing aqueous solution has a pH value <1.

9. Method according to claim 1 wherein mineralized water is used for the preparation of the sulfations-containing aqueous solution.

10. Method according to claim 1 wherein the chlorine-dioxide-containing aqueous solution contains a water-soluble phosphate.

11. Method according to claim 1 wherein the sulfations-containing aqueous solution is mixed with a therein stable peroxy compound and said solution is subsequently mixed with the aqueous alkaline solution of a chlorite in an amount such that the pH value adjusts from about 7.0 to about 8.0.

12. Method according to claim 1, wherein said aqueous medium includes sodium thiosulfate having a concentration ratio of sodium thiosulfate to chlorine dioxide on the order of 3.0 grams thiosulfate to 1.0 gram chlorine dioxide.

13. Method for flushing particle-bearing filter beds located in circuit or linear water treatment plants for sterilization and decontamination of said filter beds, wherein the filter is charged with a chlorine dioxide containing aqueous solution, which acts on the deposits of the particle-type filter bed with said bed thereafter being subsequently flushed with water and/or an aqueous medium for removal of the process-caused reaction products and any residual chlorine dioxides;

wherein the chlorine-dioxide aqueous solution charges the filter and acts upon the deposits of the particle-type filter bed for at least five minutes prior to said flushing;

wherein the particle-bearing filter bed involves single-/multi-layer filters, which contain quartz, gravel, and/or sand, and/or porous filter materials, in particular fire brick mortar and/or zeolites, and/or carbon-containing materials, in particular activated coal, lignite and/or anthracite coal; and, wherein tetra-chlorine-deca-oxide-complex-dianion $[Cl_4O_{10}]^{2-}$ is present in the chlorine dioxide-containing aqueous solution and is in equilibrium with said chlorine dioxide such that said chlorine dioxide is formed during consumption from said aqueous solution.

14. Method according to claim 13 wherein the sulfations-containing aqueous solution is mixed with a therein stable peroxy compound and said solution is subsequently mixed with the aqueous alkaline solution of a chlorite in an amount such that the pH value adjusts from about 7.0 to about 8.0.

15. Method for flushing particle-bearing filter beds located in circuit or linear water treatment plants for sterilization and decontamination of said filter beds, wherein the filter is charged with a chlorine dioxide and tetra-chlorine-deca-oxide-complex-dianion $[Cl_4O_{10}]^{2-}$ containing aqueous solution;

said tetra-chlorine-deca-oxide-complex-dianion $[Cl_4O_{10}]^{2-}$ is in equilibrium with said chlorine dioxide such that said chlorine dioxide is formed during consumption from said aqueous solution;

said chlorine dioxide-containing aqueous solution is obtained in that a sulfations-containing aqueous solution having a pH value less than or equal to 3 is mixed with a therein stable peroxy compound and said solution is subsequently mixed with the aqueous alkaline solution of a chlorite in an amount such that the pH value adjusts from about 7.0 to about 8.0;

said chlorine dioxide-containing aqueous solution is allowed to act on the sediments of the particle-type filter bed for at least one hour with said bed being subsequently flushed with water and/or an aqueous medium for removal of the process-caused reaction products and any residual chlorine dioxides; and, the particle-bearing filter bed involves single-/multi-layer filters, which contain quartz, gravel, sand, porous filter materials, and/or carbonaceous materials.

16. Method according to claim 15, wherein said aqueous medium includes sodium thiosulfate having a concentration ratio of sodium thiosulfate to chlorine dioxide on the order of 3.0 grams thiosulfate to 1.0 gram chlorine dioxide.

* * * * *